United States Patent
Christopherson et al.

(10) Patent No.: US 7,236,834 B2
(45) Date of Patent: Jun. 26, 2007

(54) ELECTRICAL LEAD BODY INCLUDING AN IN-LINE HERMETIC ELECTRONIC PACKAGE AND IMPLANTABLE MEDICAL DEVICE USING THE SAME

(75) Inventors: Mark A. Christopherson, Shoreview, MN (US); Jeff Jelen, New Hope, MN (US); Beth Anne H. Guck, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 394 days.

(21) Appl. No.: 10/742,732

(22) Filed: Dec. 19, 2003
(Under 37 CFR 1.47)

(65) Prior Publication Data
US 2005/0137670 A1 Jun. 23, 2005

(51) Int. Cl.
*A61N 1/05* (2006.01)

(52) U.S. Cl. ............................ 607/116; 607/3; 607/119; 607/120; 607/122

(58) Field of Classification Search ................ 607/122, 607/116, 119–120, 3
See application file for complete search history.

(56) References Cited

U.S. PATENT DOCUMENTS

| | | | |
|---|---|---|---|
| 4,595,009 A | 6/1986 | Leinders | |
| 4,791,935 A | 12/1988 | Baudino et al. | |
| 5,178,161 A | 1/1993 | Kovacs | |
| 5,275,171 A | 1/1994 | Barcel | |
| 5,280,413 A | 1/1994 | Pai | |
| 5,281,219 A | 1/1994 | Kallok | |
| 5,314,495 A | 5/1994 | Kovacs | |
| 5,325,870 A | 7/1994 | Kroll et al. | |
| 5,336,253 A | 8/1994 | Gordon et al. | |
| 5,411,532 A | 5/1995 | Mortazavi | |
| 5,423,873 A | 6/1995 | Neubauer et al. | |
| 5,458,631 A * | 10/1995 | Xavier | 607/117 |
| 5,470,345 A | 11/1995 | Hassler et al. | |
| 5,490,323 A * | 2/1996 | Thacker et al. | 29/825 |
| 5,501,703 A | 3/1996 | Holsheimer et al. | |
| 5,513,793 A | 5/1996 | Malmgren | |
| 5,571,156 A | 11/1996 | Schmukler | |
| 5,593,430 A | 1/1997 | Renger | |
| 5,620,476 A | 4/1997 | Truex et al. | |

(Continued)

FOREIGN PATENT DOCUMENTS

EP 0 844 899 B1 7/2003

(Continued)

*Primary Examiner*—Robert Pezzuto
*Assistant Examiner*—Shevon Johnson
(74) *Attorney, Agent, or Firm*—Ingrassia, Fisher & Lorenz, P.C.

(57) ABSTRACT

An assembly is provided for an implantable medical lead. The assembly includes a first lead body comprising one or more electrical leads, and a hermetic encasement. The encasement comprises a housing having first and second openings and interior walls, an interior space defined by the interior walls, an electronic network housed within the interior space, and a circuit board extending through the first and second openings. The circuit board comprises a plurality of layers into which the electronic network is at least partially integrated, a first set of one or more terminals electrically coupling the electronic network to the first lead body, and a second set of one or more terminals electrically coupled to the electronic network for external electrical engagement.

29 Claims, 6 Drawing Sheets

U.S. PATENT DOCUMENTS

| | | | |
|---|---|---|---|
| 5,643,330 A | 7/1997 | Holsheimer et al. | |
| 5,679,022 A * | 10/1997 | Cappa et al. | 439/502 |
| 5,683,435 A | 11/1997 | Truex et al. | |
| 5,738,270 A | 4/1998 | Malmgren | |
| 5,782,798 A * | 7/1998 | Rise | 604/500 |
| 5,782,891 A | 7/1998 | Hassler et al. | |
| 5,843,135 A | 12/1998 | Weijand et al. | |
| 5,904,708 A * | 5/1999 | Goedeke | 607/18 |
| 5,925,070 A | 7/1999 | King et al. | |
| 5,935,155 A | 8/1999 | Humayun et al. | |
| 5,999,848 A | 12/1999 | Gord et al. | |
| 6,011,993 A | 1/2000 | Tziviskos et al. | |
| 6,038,480 A | 3/2000 | Hrdlicka et al. | |
| 6,052,623 A | 4/2000 | Fenner et al. | |
| 6,062,902 A * | 5/2000 | Buckles et al. | 439/502 |
| 6,083,252 A | 7/2000 | King et al. | |
| 6,163,723 A | 12/2000 | Roberts et al. | |
| 6,192,279 B1 * | 2/2001 | Barreras et al. | 607/117 |
| 6,411,854 B1 | 6/2002 | Tziviskos et al. | |
| 6,414,835 B1 | 7/2002 | Wolf et al. | |
| 6,418,348 B1 | 7/2002 | Witte | |
| 6,421,566 B1 | 7/2002 | Holsheimer | |
| 6,473,653 B1 | 10/2002 | Schallhorn et al. | |
| 2002/0128694 A1 | 9/2002 | Holsheimer | |
| 2003/0093130 A1 | 5/2003 | Stypulkowski | |

FOREIGN PATENT DOCUMENTS

| | | |
|---|---|---|
| GB | 2 124 495 A | 2/1984 |
| GB | 2 134 335 A | 8/1984 |
| GB | 2 166 606 A | 10/1985 |
| WO | WO95 19804 A1 | 7/1995 |
| WO | WO97 06853 A1 | 2/1997 |
| WO | WO97 20332 A1 | 6/1997 |
| WO | WO97 37720 A1 | 10/1997 |
| WO | WO97 38752 A2 | 10/1997 |
| WO | WO97 38752 A3 | 10/1997 |
| WO | WO99 06105 A1 | 2/1999 |
| WO | WO99 45870 A1 | 9/1999 |
| WO | WO99 49934 A1 | 10/1999 |
| WO | WO00 56677 A1 | 9/2000 |
| WO | WO03 003791 A1 | 1/2003 |
| WO | WO03 033070 A1 | 4/2003 |
| WO | WO03 041795 A1 | 5/2003 |
| WO | WO03 092807 A1 | 11/2003 |

* cited by examiner

ELECTRICAL LEAD BODY INCLUDING AN IN-LINE HERMETIC ELECTRONIC PACKAGE AND IMPLANTABLE MEDICAL DEVICE USING THE SAME

TECHNICAL FIELD

The present invention generally relates to electrical lead bodies, and more particularly relates to the application of electrical lead bodies with implantable medical devices and small hermetic electronic enclosures.

BACKGROUND

An implantable medical device (IMD) is an apparatus that during use is placed inside a living body to monitor certain physiological signals and provide therapy to an organ or tissue in response to the physiological signals. An example of an IMD is an implantable cardiac device (ICD) such as a pacemaker that stimulates the heart into a contraction if the sinus node is not properly pacing such contractions. Modem cardiac devices also perform many functions beyond that of pacing. For example, some ICDs perform defibrillation and cardioversion therapies. Other ICDs are able to select among several different pacing therapies depending upon the physiologic condition of a patient's heart.

A pacemaker device, as an example of an ICD, is typically implanted in a convenient location such as beneath a patient's skin and in the vicinity of the one or more major arteries or veins. One or more electrical leads connected to the pacemaker are typically placed on or inside the patient's heart via a convenient artery or vein. The ends of the leads are placed in contact with the inside walls or the surface of one or more chambers of the heart, depending upon the particular therapies deemed appropriate for the patient.

One or more leads are adapted to carry a current from the pacemaker to the heart tissue to stimulate the heart in one of several ways, again depending upon the particular therapy being delivered. The leads are also used for sensing the physiologic signals provided by the heart to determine when to deliver a therapeutic pulse to the heart, and the nature of the pulse, e.g., a pacing pulse or a defibrillation shock. In other types of IMDs or implantable systems, additional leads may be used for applying a pain therapy stimulus to various body areas such as the spinal column. Further, one or more catheters may be connected to the IMD to deliver drugs to various body parts for pain relief, defibrillation threshold reduction, and so forth.

Distributing a variety of leads, catheters, and medical activators about a patient's body from a single IMD is a very complex procedure. Further, many lead conductors and connections to the IMD are required in order for many electrodes to be distributed. Leads and connections are expensive and increase the overall IMD size. Further, as the number of leads extending from a central device increases, the overall system reliability is reduced.

Accordingly, it is desirable to provide a simple and cost efficient system for distributing leads and associated medical activators from an IMD to one or more body locus. In addition, it is desirable to reduce the number of components associated with an IMD and thereby improve the reliability of the IMD and the associated system. Furthermore, other desirable features and characteristics of the present invention will become apparent from the subsequent detailed description and the appended claims, taken in conjunction with the accompanying drawings and the foregoing technical field and background.

BRIEF SUMMARY

An assembly is provided for an implantable medical lead. The assembly includes a first lead body comprising one or more electrical leads, and a hermetic encasement. The encasement comprises a housing having first and second openings and interior walls, an interior space defined by the interior walls, an electronic network housed within the interior space, and a circuit board extending through the first and second openings. The circuit board comprises a plurality of layers into which the electronic network is at least partially integrated, a first set of one or more terminals electrically coupling the electronic network to the first lead body, and a second set of one or more terminals electrically coupled to the electronic network for external electrical engagement.

An implantable package is also provided for conducting electrical energy between an implantable medical device and a medical activator unit. The package comprises a housing having first and second openings and interior walls, an interior space defined by the interior walls, an electronic network housed within the interior space, and a circuit board extending through the first and second openings. The circuit board comprises a plurality of layers into which the electronic network is at least partially integrated, a first set of one or more terminals for electrically coupling the electronic network to the implantable medical device, and a second set of one or more terminals electrically coupled to the electronic network for external electrical engagement with the at least one medical activator unit.

An implantable medical device is also provided. The device comprises a controlling device having an electrical output for transmitting command signals, a first lead body comprising one or more electrical leads, and a hermetic encasement. The encasement comprises a housing having first and second openings and interior walls, an interior space defined by the interior walls, an electronic network housed within the interior space, and a circuit board extending through the first and second openings. The circuit board comprises a plurality of layers into which the electronic network is at least partially integrated, a first set of one or more terminals electrically coupling the electronic network to the first lead body, and a second set of one or more terminals electrically coupled to the electronic network for external electrical engagement.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
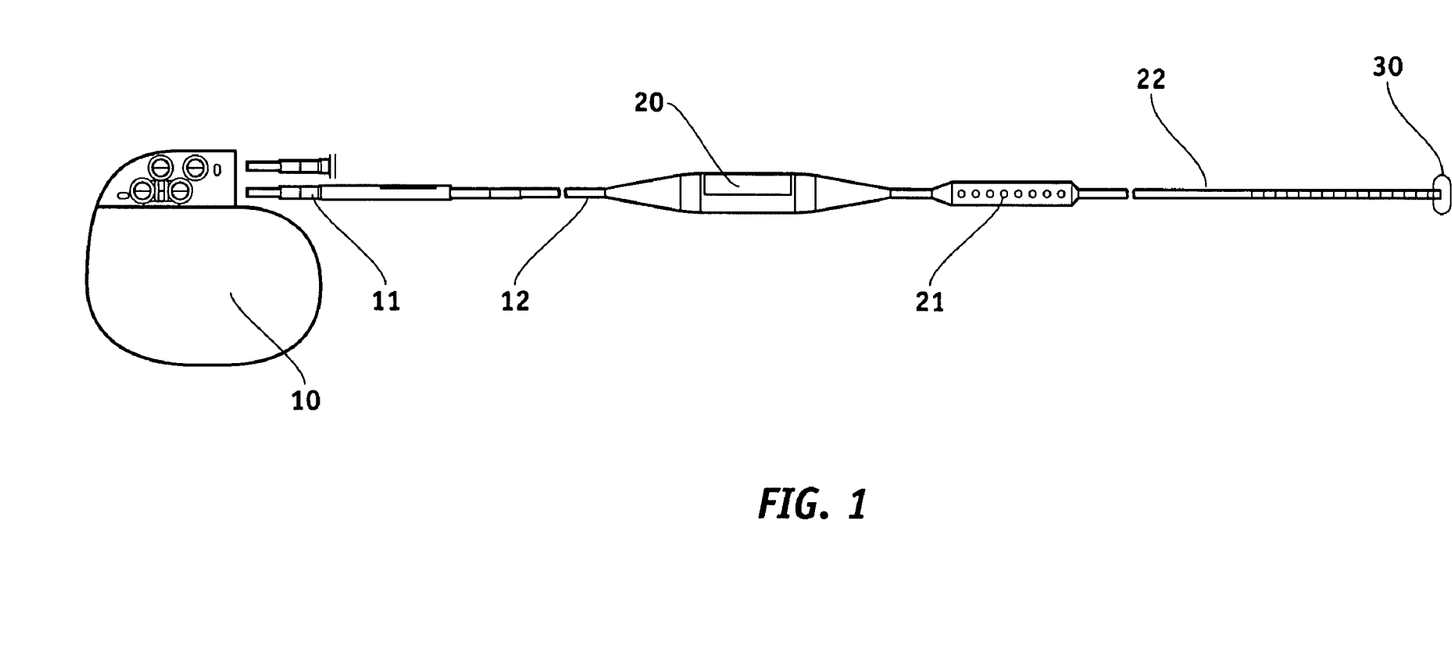
FIG. 1 is a side view of a medical device assembly according to an embodiment of the present invention including a medical device, a first lead body, an in-line hermetic encasement, and a second lead body.

For convenience, unless otherwise indicated the term "IMD" is inclusive of any implantable medical device capable of administering any of a number of therapies to the heart or other organs or other tissue of the patient. FIG. 1 illustrates an embodiment of the present invention in the context of a cardiac pacemaker, it being understood that the invention certainly has applicability to many other types of IMDs. For example, while the present invention will be described with reference to the use of medical electrical leads having electrodes that monitor or treat a heart, it will be appreciated that the present invention may be used in conjunction with any suitable medical lead having a sensor, stimulator or other treatment device adapted for a sensing and/or treatment application. For convenience, all types of such sensors, stimulators and treatment devices will be referred to herein as "medical activator units." Examples of suitable medical activator units include mechanical sensors, such as, for example, thermocouples, strain gauges, sonomicrometers and accelerometers, biosensors, such as calcium or other chemical sensors, drug-delivery systems, and the like.

As depicted in FIG. 1, one or more leads collectively identified as lead body 11 are electrically coupled to a medical device 10 that is implanted at a medically suitable location in a patient's body during use. The lead body 11 extends to another suitable location in the patient's body where it is electrically coupled to a hermetic electronic encasement 20. The lead body 11 may directly engage with the encasement 20. Alternatively, the lead body 11 may indirectly engage with the encasement 20 via a "smart extension" 12 that directly engages with the encasement 20 at one end and engages with the lead body 11 at an opposite end. The encasement 20 houses an electronic network that may include a memory for storing programs that, when carried out, enable the electronic network to communicate with and control multiple medical activator units, although only one such unit 30 is shown in FIG. 1. The encasement 20 may further include at least one energy source 32 such as a battery to power the electronic network and the medical activator units 30. The encasement 20 and its contents will be described in greater detail below.

A plurality of leads collectively identified as lead body 22 are electrically coupled to the encasement 20 at one end and are directly engaged or indirectly coupled with the medical activator units at an opposite end. Optionally, a connector block 21 can be fastened to the encasement 20. The connector block 21 electrically connects one or more leads to the encasement 20 via connectors such as lead clamps (not shown) that hold the leads in place using tightening set screws or other suitable securing devices.

Figure 2:
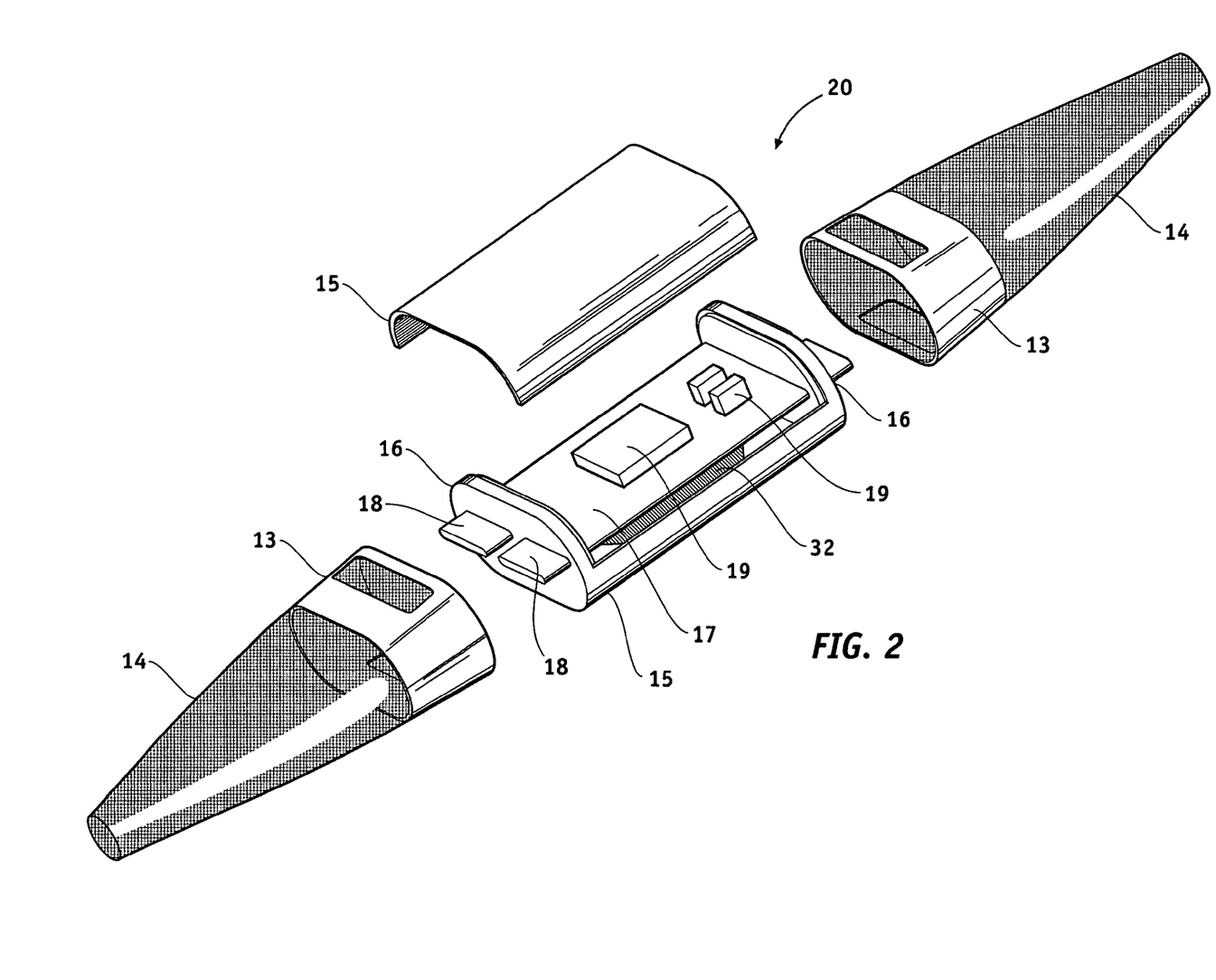
FIG. 2 is an isometric view of the components of a hermetic encasement according to an embodiment of the present invention.
Figure 3:
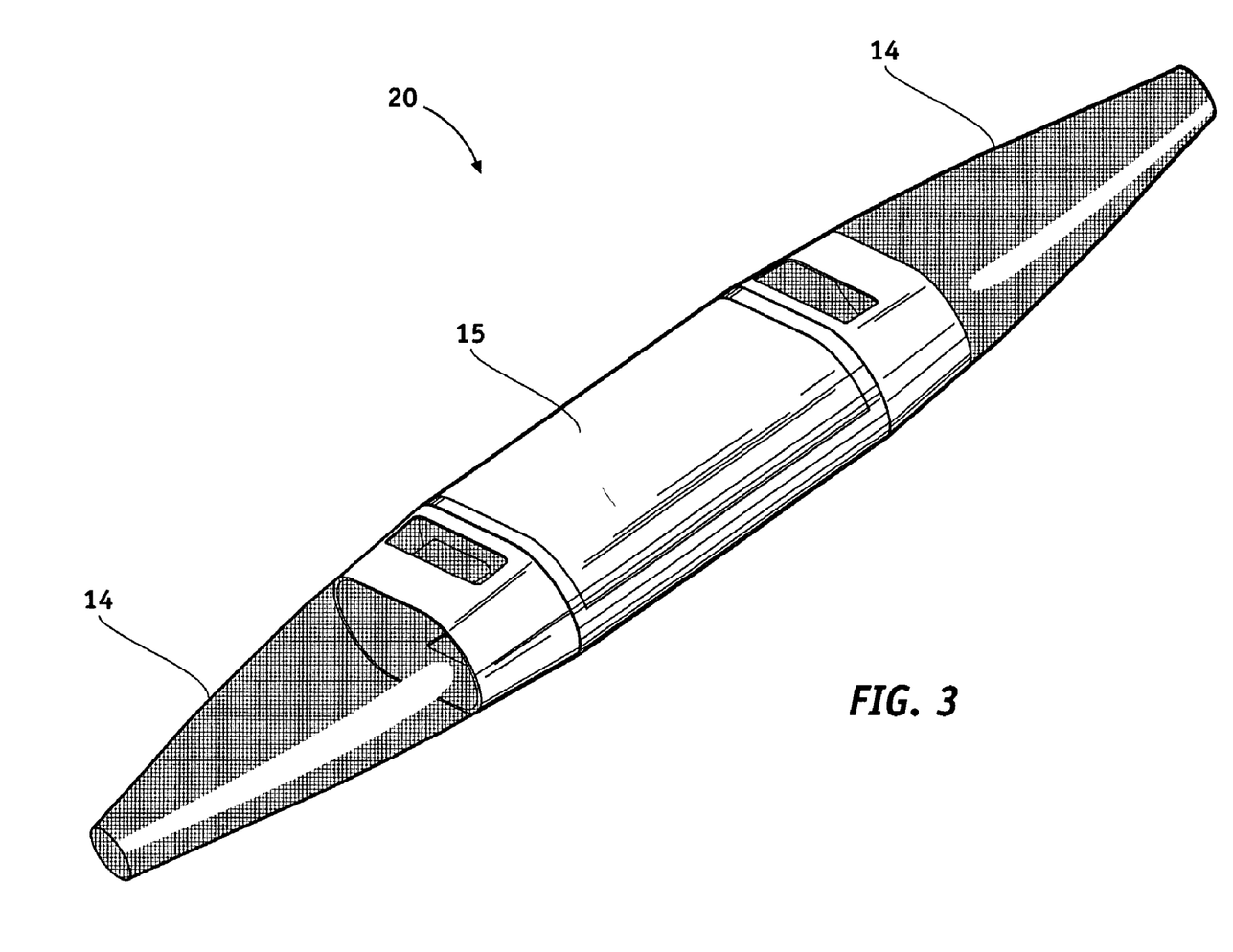
FIG. 3 is an isometric view of the hermetic encasement of FIG. 2 in an assembled condition.

FIGS. 2 and 3 respectively depict an unassembled and assembled hermetic electronic encasement 20. As mentioned above, the encasement 20 serves as the housing for electronic intelligence and other components such as at least one energy source 32, and integrated electrical circuitry/components 19 that may include stand-alone therapeutic devices that operate in an independent and self-contained manner. The encasement 20 is in-line with the lead bodies 11, 22 and consequently enables both stand-alone devices and components that are controlled by the medical device 10 to be disposed downstream from and in direct communication with the medical device 10.

Although the energy source 32 may be a simple battery, the hermetic encasement 20 may be powered by dedicated conductive lines from the IMD. In another embodiment, the energy source 32 harvests or rectifies power from the IMD stimulation pulses and stores the same in order to power the hermetic encasement 20. In yet another embodiment, the hermetic encasement 20 is temporarily powered via an external magnetic field or RF energy.

The electrical circuitry/components 19 are integrated into or mounted onto a multi-layered circuit board 17 formed of biostable materials. In an exemplary embodiment of the invention the circuit board 17 is a multi-layered ceramic structure that includes surface bonding pads 18 for coupling the circuitry/components 19 to the lead bodies 11, 22. The bonding pads 18 are deposited onto the circuit board 17 using any conventional depositing method and are formed from a biocompatible metal such as gold or platinum. Examples of depositing techniques include printing, chemical vapor deposition, or physical deposition such as sputtering.

Figure 6:
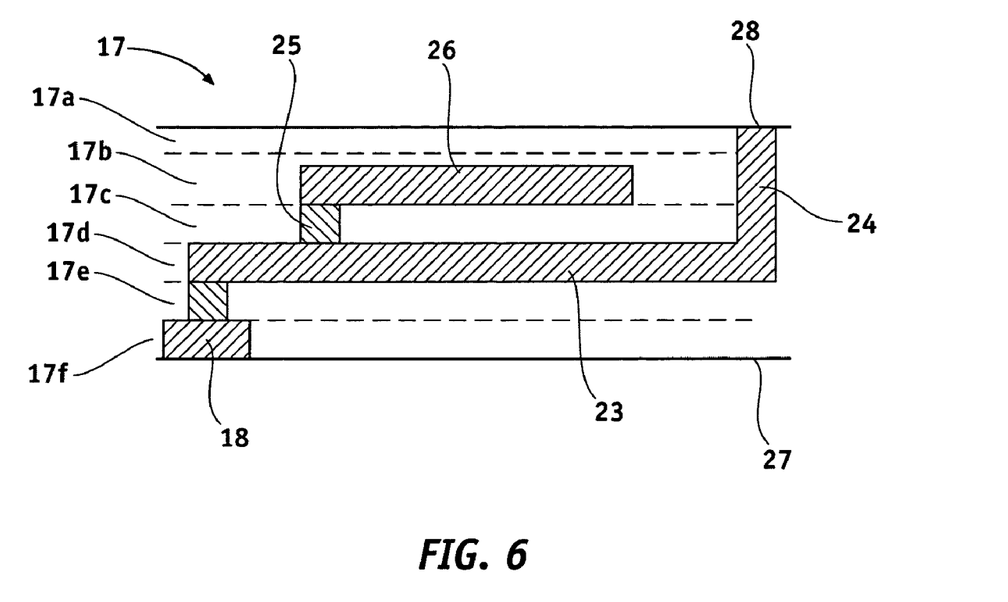
FIG. 6 is a cross sectional view of a circuit board adapted to be encased in the hermetic encasement according to an embodiment of the present invention.

FIG. 6 is a cross-sectional view of the circuit board 17 and exemplary circuitry, including an electrical pathway between one surface 28 on which electrical components may be mounted and a bonding pad 18 deposited on an opposite surface 27. In the embodiment depicted in FIG. 6 the circuit board 17 is a structure of six layers 17a–17f formed from any suitable biocompatible ceramic materials including but not limited to aluminum oxide. The ceramic material forming each of the layers in the circuit board 17 is between about 92% and 99.8% aluminum oxide. The embedded and exposed conductors forming a circuit can be any suitable metal including but not limited to platinum, gold, tungsten, moly-manganese, and alloys of such metals and metal compounds. The circuitry includes intra-layer pathways 23, 26 and interlayer pathways 24, 25 and forms a network that can be populated with interconnects, resistors, capacitors, surface components on either surface 27, 28, and so forth.

Figure 4:
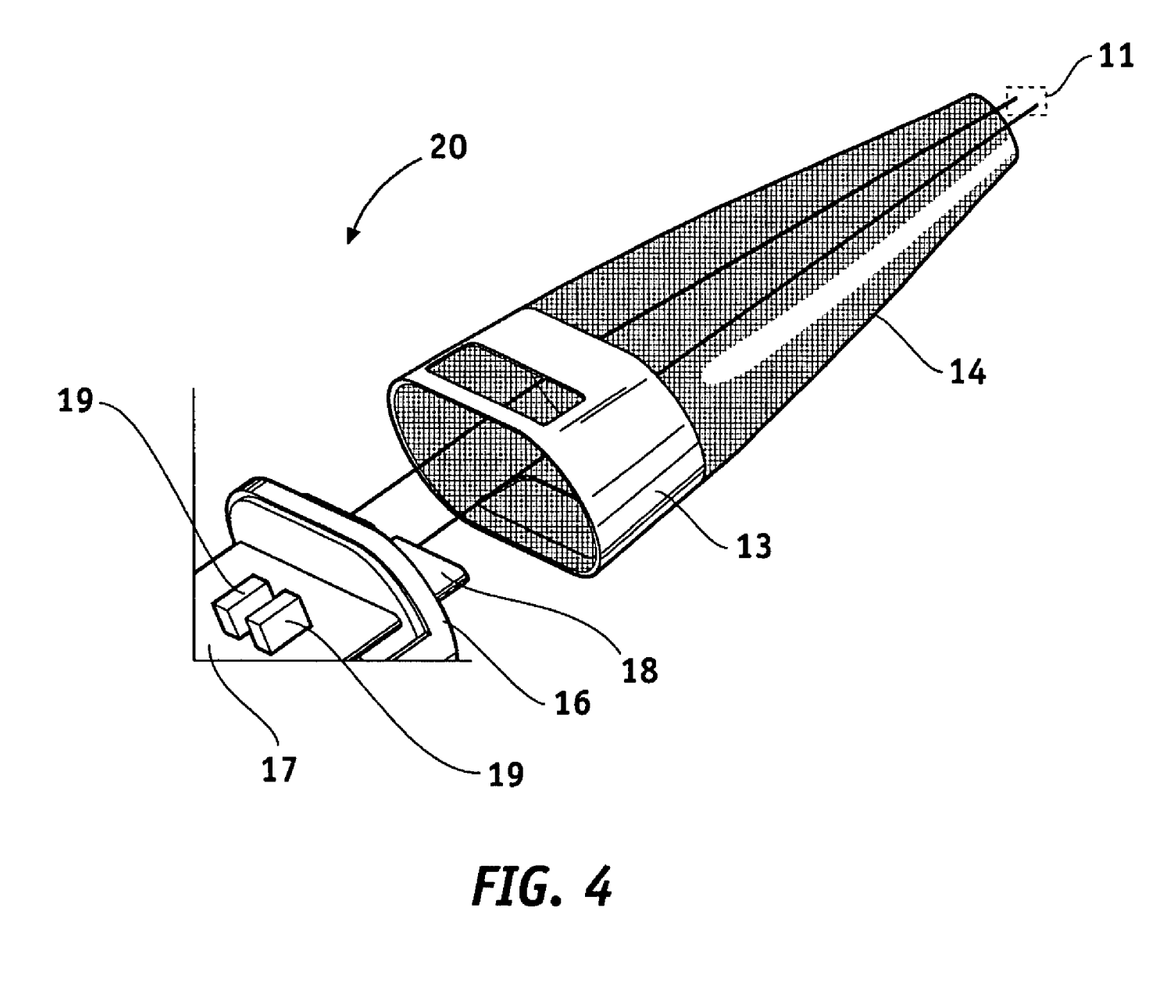
FIG. 4 is an isometric view of an input side of the hermetic encasement of FIG. 2 and associated leads.
Figure 7:
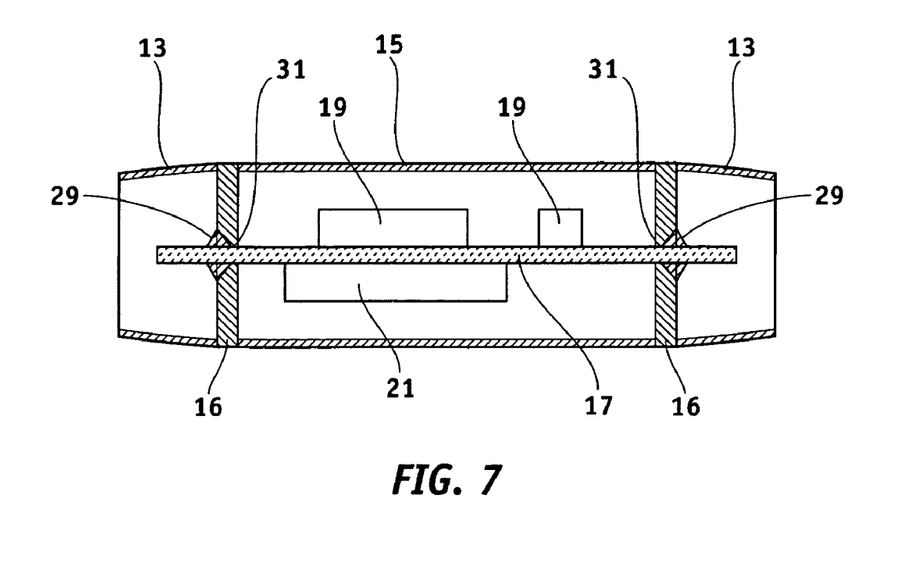
FIG. 7 is a cross sectional view of the hermetic encasement of FIG. 2.

Returning now to the exterior components of the hermetic electronic encasement 20, FIGS. 3 and 4 depict the encasement assembly including side walls 15 that combine to surround the mid-portion of the circuit board 17, and end walls 16 that are attached to the side walls to complete the encasement 20. In an exemplary embodiment of the invention, the end walls 16 and side walls are composed of a ceramic material that includes one or more of titanium, niobium, or niobium 46-titanium. The ceramic material is preferably formed in layers, including integral layers of dielectric material for EMI shielding. FIG. 7 is a cross sectional view of the hermetic electronic encasement 20, and illustrates the circuit board 17 extending through openings 31 in each of the end walls 16. A braze material 29 is applied at the circuit board/end plate interfaces in order to provide a hermetic seal at the interface. With the circuit board ends disposed outside the encasement 20 the bonding pads 18 are exposed to the encasement exterior, thereby allowing lead bodies 11, 22 to be coupled to the bonding pads 18. The end walls 16 can be joined to the side walls 15 using any conventional joining method, preferably using a laser, furnace, or thermo-compression micro-joining process. In an exemplary embodiment of the invention, the end walls 16 and the side walls 15 are connected using a micro-joining material such as gold, indium, active gold braze alloys, platinum alloys, titanium-copper-nickel active brazes, or at least one biocompatible sealing glass composition.

Figure 5:
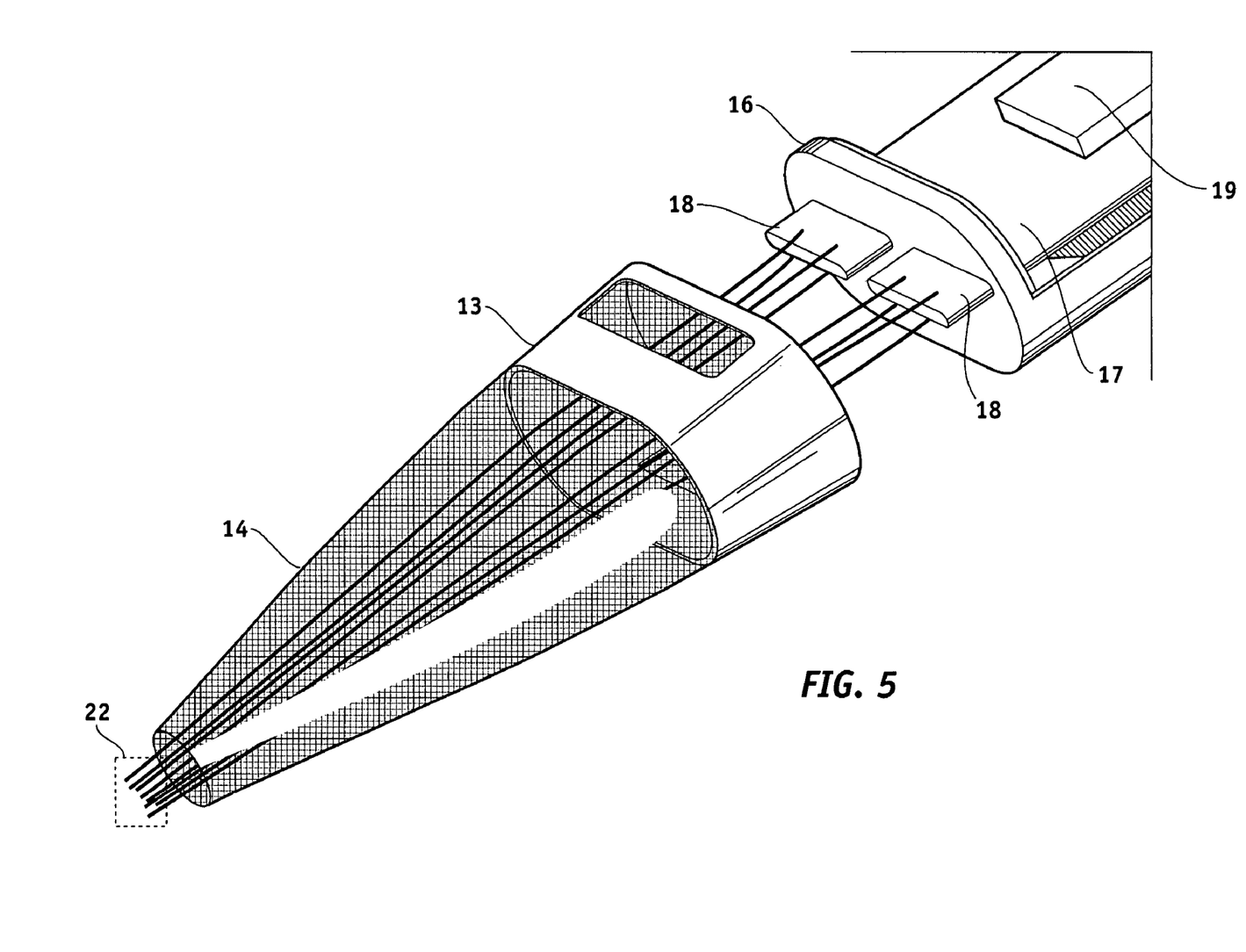
FIG. 5 is an isometric view of an output side of the hermetic encasement of FIG. 2 and associated leads.

In order to protect and maintain the connections between the bonding pads 18 and the lead bodies 11, 22 a flexible strain relief device 14 can be attached to one or both of the encasement ends. FIGS. 4 and 5 provide close-up illustrations of identical shrouds, each of which being an exemplary flexible strain relief device 14. FIG. 4 depicts the output side of the encasement 20 and its associated lead body 22, and FIG. 5 depicts the input side together with its associated lead body 11. An adaptor 13 can be coupled to the strain relief device 14 to appropriately shape the device 14 and provide rigidity to the portion of the device 14 that interfaces with an endplate 16.

One exemplary application of a lead assembly that includes an in-line hermetic encasement is a neurological stimulator lead system. In such a system, package-integrated high density inputs/outputs are mounted onto the circuit board 17 and an electrode multiplexer selectively carries out coordinated signals to an array of electrodes that apply currents to nerves or other body tissues. Because the electronic encasement is disposed in-line with the lead bodies, more electrodes can originate from a downstream point relative to a device 10 instead of originating from the device 10 itself. Further, the in-line encasement 20 contains circuitry that would conventionally be disposed in the device 10. These advantages allow the device to be much smaller due to a limited amount of circuitry and output ports required by the device 10. Additionally, the in-line encasement is small enough to be disposed in main arteries or other small passageways in a patient.

Communication components including receivers, transmitters, and associated circuitry are enclosed within the encasement to enable external interaction with the electronic intelligence in the hermetic encasement 20. A user may optimize current vectors to the tissue by programming the electronic intelligence in advance to select different electrode configurations. During a treatment, the user may further optimize current vectors by transmitting command signals to the communication circuitry. Alternatively, the device 10 may automatically control the circuitry 19 within the encasement 20. The communication circuitry may receive programming or other commands directly from a user-controlled external device, or indirectly via the device 10. In an exemplary embodiment of the invention the programming or other commands are transmitted to the communication circuitry by wireless means, although it is clearly within the scope of the invention for communication signals to also be sent via a dedicated communication line, or modulated on top of a dedicated power line. For instance, pulse patterns that are provided as part of therapy stimulation may be used to program or control the circuitry 19, or communication signals of very small amplitude may be modulated on top of such power or therapy signals.

A similar exemplary application includes a cardiac padding lead with multiple ring electrodes that that are individually controlled and operated and allow for varied ring-tip separation. Another similar exemplary application of the present invention includes a multiple physiologic sensor array (EcOG) for treating epilepsy, for example. In this or other embodiments, a drug pump may be among the electrical components 19 mounted onto the circuit board 17. At least one catheter extending through the encasement 20 and in fluid communication with the pump would deliver drugs to targeted areas.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An assembly for an implantable medical lead, comprising:
    a first lead body comprising one or more electrical leads; and
    a hermetic encasement, comprising:
        a housing having first and second openings and interior walls, an interior space defined by said interior walls, an electronic network housed within said interior space, and a circuit board extending through said first and second openings, comprising:
            a plurality of layers into which said electronic network is at least partially integrated, a first set of one or more terminals electrically coupling said electronic network to said first lead body, and a second set of one or more terminals electrically coupled to said electronic network for external electrical engagement.

2. An assembly according to claim 1, further comprising:
    a second lead body comprising at least two electrical leads, each lead in said second lead body being electrically coupled to one of said terminals in said second set.

3. An assembly according to claim 2, wherein each lead in said second lead body is further electrically coupled to a medical activator unit selected from the group consisting of a thermocouple, a strain gauge, a sonomicrometer, an accelerometer, a biosensor, and a drug-delivery device.

4. An assembly according to claim 3, wherein said second lead body comprises more leads than said first lead body.

5. An assembly according to claim 1, wherein said plurality of layers comprise a ceramic material.

6. An assembly according to claim 1, wherein said circuit board comprises surface mount pads, each of said surface mount pads being electrically coupled to one of said terminals.

7. An assembly according to claim 1, wherein said ceramic material comprises between about 92% and about 99.8% aluminum oxide.

8. An assembly according to claim 1, wherein said hermetic encasement further comprises a drug delivery device responsive to said electronic network, and a catheter extending through said housing and in fluid communication with said fluid pump.

9. An assembly according to claim 1, wherein said hermetic encasement further comprises an energy source for providing power at least to said electronic network.

10. An assembly according to claim 1, wherein said hermetic encasement further comprises a transmitter and a receiver for transmitting and receiving command signals external to said hermetic encasement, said transmitter and receiver being in electrical communication with said electronic network.

11. An implantable package for conducting electrical energy between an implantable medical device and at least one medical activator unit, comprising:
- a housing having first and second openings and interior walls;
- an interior space defined by said interior walls;
- an electronic network housed within said interior space; and
- a circuit board extending through said first and second openings, comprising:
  - a plurality of layers into which said electronic network is at least partially integrated, a first set of one or more terminals for electrically coupling said electronic network to said implantable medical device, and a second set of one or more terminals electrically coupled to said electronic network for external electrical engagement with said at least one medical activator unit.

12. A package according to claim 11, wherein said plurality of layers comprise a ceramic material.

13. A package according to claim 11, wherein said circuit board comprises surface mount pads, each of said surface mount pads being electrically coupled to one of said terminals.

14. A package according to claim 11, wherein said ceramic material comprises between about 92% and about 99.8% aluminum oxide.

15. A package according to claim 11, wherein said hermetic encasement further comprises a drug delivery device responsive to said electronic network, and a catheter extending through said housing and in fluid communication with said fluid pump.

16. A package according to claim 11, wherein said hermetic encasement further comprises an energy source for providing power at least to said electronic network.

17. A package according to claim 11, wherein said hermetic encasement further comprises a transmitter and a receiver for transmitting and receiving command signals external to said hermetic encasement, said transmitter and receiver being in electrical communication with said electronic network.

18. An implantable medical device, comprising:
- a controlling device for transmitting command signals, said controlling device comprising an electrical output;
- a first lead body comprising one or more electrical leads, said first lead body having a first end and a second end, said first end being coupled to said electrical output; and
- a hermetic encasement, comprising:
  - a housing having first and second openings and interior walls, an interior space defined by said interior walls, an electronic network housed within said interior space, and a circuit board extending through said first and second openings, comprising:
    - a plurality of layers into which said electronic network is at least partially integrated, a first set of one or more terminals electrically coupling said electronic network to said first lead body, and a second set of one or more terminals electrically coupled to said electronic network for external electrical engagement.

19. A device according to claim 18, wherein said plurality of layers comprise a ceramic material.

20. A device according to claim 18, further comprising:
- a second lead body comprising at least two electrical leads, each lead in said second lead body being electrically coupled to one of said terminals in said second set.

21. A device according to claim 20, wherein each lead in said second lead body is further electrically coupled to a medical activator unit selected from the group consisting of a thermocouple, a strain gauge, a sonomicrometer, an accelerometer, a biosensor, and a drug-delivery device.

22. A device according to claim 20, wherein said second lead body comprises more leads than said first lead body.

23. A device according to claim 18, wherein said circuit board comprises surface mount pads, each of said surface mount pads being electrically coupled to one of said terminals.

24. A device according to claim 18, wherein said ceramic material comprises between about 92% and about 99.8% aluminum oxide.

25. A device according to claim 18, wherein said hermetic encasement further comprises a drug delivery device responsive to said electronic network, and a catheter extending through said housing and in fluid communication with said fluid pump.

26. A device according to claim 18, wherein said hermetic encasement further comprises an energy source for providing power at least to said electronic network.

27. A device according to claim 18, wherein said hermetic encasement further comprises a transmitter and a receiver for transmitting and receiving command signals external to said hermetic encasement, said transmitter and receiver being in electrical communication with said electronic network.

28. A device according to claim 1, further comprising a first strain relief device coupled to an end of said housing.

29. A device according to claim 28 wherein said strain relief comprises a shroud disposed over said first set of terminals.

* * * * *